US009234177B2

(12) United States Patent
Tzu-Bi Shih et al.

(10) Patent No.: US 9,234,177 B2
(45) Date of Patent: Jan. 12, 2016

(54) HUMAN MULTIPOTENT EMBRYONIC STEM CELL-LIKE PROGENITOR CELLS

(75) Inventors: Daniel Tzu-Bi Shih, Lake Oswego, OR (US); Ming-Song Tsai, Taipei (TW)

(73) Assignee: SUNSHINE LIFE SCIENCE & TECHNOLOGY CORP., New Taipei (TW)

(*) Notice: Subject to any disclaimer, the term of this patent is extended or adjusted under 35 U.S.C. 154(b) by 511 days.

(21) Appl. No.: 13/276,106

(22) Filed: Oct. 18, 2011

(65) Prior Publication Data

US 2012/0094380 A1    Apr. 19, 2012

Related U.S. Application Data

(60) Provisional application No. 61/394,073, filed on Oct. 18, 2010.

(51) Int. Cl.
*C12N 5/0775* (2010.01)
*C12N 5/073* (2010.01)

(52) U.S. Cl.
CPC ............ *C12N 5/0668* (2013.01); *C12N 5/0605* (2013.01)

(58) Field of Classification Search
CPC .. C12N 5/0605; C12N 5/0668; C12N 5/0667; C12N 5/0663; C12N 5/0632; C12N 5/0607; C12N 5/0675; C12N 5/0682; C12N 2501/39; C12N 2501/10; A61K 2035/124; A61K 35/12; C07K 14/705; A61L 27/3834
See application file for complete search history.

(56) References Cited

U.S. PATENT DOCUMENTS

| 2007/0122903 A1 | 5/2007 | Rezania et al. |
| 2008/0044900 A1* | 2/2008 | Mooney et al. ............... 435/375 |
| 2008/0213228 A1 | 9/2008 | Edinger et al. |
| 2008/0241171 A1 | 10/2008 | Gentry et al. |
| 2010/0124569 A1 | 5/2010 | Abbot et al. |

FOREIGN PATENT DOCUMENTS

| EP | 1605040 A1 | 12/2005 |
| WO | 2008/036374 A2 | 3/2008 |
| WO | 2009/044379 A2 | 4/2009 |
| WO | WO 2009/045201 A1 | 4/2009 |

OTHER PUBLICATIONS

Dev Mittar, Rosanto Paramban, and Catherine McIntyre, Flow Cytometry and High-Content Imaging to Identify Markers of Monocyte-Macrophage Differentiation, 2011, BD Biosciences Application Note, pp. 1-20.*

(Continued)

*Primary Examiner* — Ralph Gitomer
*Assistant Examiner* — Trent Clarke
(74) *Attorney, Agent, or Firm* — Ditthavong & Steiner, P.C.

(57) ABSTRACT

The invention provides a plurality of embryonic stem cell-like progenitor cells, which are isolated from a human tissue by a systemic screening of human mesenchymal stromal stem/progenitor cells and a cell sorting by a cell antigen selected from the group consisting of CD34, CD117, CD133, CD201, GloboH and combination thereof, and cultured in a medium supplemented with at least one or more steroids and one or more growth factors. The cells of the invention express CD34 and exhibit sphere-like clonogenicity in early passages and express multipotent embryonic stem cells (ESCs) like characteristics.

2 Claims, 7 Drawing Sheets

(A)

(B)

(56) References Cited

OTHER PUBLICATIONS

Paolo De Coppi, Georg Bartsch, Jr, M Minhaj Siddiqui, Tao Xu, Cesar C Santos, Laura Perin, Gustavo Mostoslaysky, Angeline C Serre, Evan Y Snyder, James J Yoo, Mark E Furth, Shay Soker & Anthony Atala, Isolation of amniotic stem cell lines with potential for therapy, 2007, Nature Biotechnology, vol. 25, No. 1, pp. 100-106, published online Jan. 7, 2007.*

Webpage labeled "N-2 Supplement" accessed at http://www.invitrogen.com/site/us/en/home/support/Product-Technical-Resources/media_formulation.166.html on Aug. 8, 2013.*

Pdf labeled "Clonetics EGM-2" accessed at http://bio.lonza.com/uploads/tx_mwaxmarketingmaterial/Lonza_ManualsProductInstructions_TechSheet_-_Endothelial_Cell_Medium_Products.pdf on Aug. 8, 2103.*

Webpage labeled "FBS" accessed at http://www.labome.com/method/Fetal-Bovine-Serum.html on Aug. 8, 2013.*

Shu Zhang, Curt Balch, Michael W. Chan, et al., Identification and Characterization of Ovarian Cancer-Initiating Cells from Primary Human Tumors, Cancer Res 2008;68:4311-4320.*

NPL pdf document "Guidance memorandum Mar. 4, 2014" accessed Mar. 27, 2014 from http://www.uspto.gov/patents/law/exam/myriad-mayo_guidance.pdf.*

Francesco De Francesco, Virginia Tirino, Vincenzo Desiderio, Giuseppe Ferraro, Francesco D'Andrea, Mariateresa Giuliano, Guido Libondi, Giuseppe Pirozzi, et al., Human CD34+/CD90+ ASCs Are Capable of Growing as Sphere Clusters, Producing High Levels of VEGF and Forming Capillaries, PLoS ONE, vol. 4:8, e6537, pp. 1-13, published online Aug. 6, 2009.*

Nadia Quirici, Cinzia Scavulio, Laura de Girolamo, Silvia Lopa, Elena Arrigoni, Giorgio Lambertenghi Deliliers, and Anna T. Brini., Anti-L-NGFR and -CD34 Monoclonal Antibodies Identify Multipotent Mesenchymal Stem Cells in Human Adipose Tissue, 2010, Stem Cells and Development, vol., 19(6), pp. 915-925, published online Nov. 23, 2009.*

Hirotaka Suga, Daisuke Matsumoto, Hitomi Eto, Keita Inoue, Noriyuki Aoi, Harunosuke Kato, Jun Araki, and Kotaro Yoshimura, Functional Implications of CD34 Expression in Human Adipose-Derived Stem/Progenitor Cells, 2009, Stem Cells and Development, 2009, vol. 18(8), pp. 1201-1210, published online Feb. 18, 2009.*

Sunghoon Jung, Krishna M. Panchalingam, Lawrence Rosenberg, and Leo A. Behie, Ex Vivo Expansion of Human Mesenchymal Stem Cells in Defined Serum-Free Media, 2012, Stem Cells International, vol. 2012, Article ID 123030, pp. 1-21.*

International Search Report for related International Application No. PCT/US2011/056737 dated Mar. 13, 2012.

J.K. Lee & J.C. Kim, "Progenitor Cells in Healing After Pterygium Excision," Yonsei Med. J. 48: 48-54 (2007).

* cited by examiner (A)

(B)

(A)

(B)

(A)

(B)

(A)

(B)

HUMAN MULTIPOTENT EMBRYONIC STEM CELL-LIKE PROGENITOR CELLS

This application claims priority to provisional application 61/394,073 filed Oct. 18, 2010.

BACKGROUND OF THE INVENTION

1. Field of the Invention

The present invention relates to a population of precursor/progenitor cells, particularly enriched with multipotent embryonic stem cell-like mesenchymal common progenitor cells (MCPCs), and method for enriching the same.

2. Description of Related Art

In regenerative medicine, to identify a source of stem cells of high safety and efficacy is the first step of the development of bio materials for repairing and renewing damaged and defective tissues. Human embryonic stem cells (hESCs) can remain undifferentiated, if cultured under appropriate conditions, and begin to spontaneously differentiate into various types of cells, which is a good indication that a culture of embryonic stem cells is a source for producing various types of cells. However, it is not an efficient way because to control the differentiation of embryonic stem cells is required (see: *Stem Cells: Scientific Progress and Future Research Directions.* Department of Health and Human Services. Jun. 2001.).

Mesenchymal stem cells, or MSCs, are multipotent stem cells that can differentiate into a variety of cell types. MSCs have been isolated from placenta, adipose tissue, lung, bone marrow, dental pulp, and blood. Cell types that MSCs have been shown to differentiate into in vitro or in vivo osteoblasts, chondrocytes, myocytes, adipocytes, and beta-pancreatic islets cells. MSCs were found to be rare in bone marrow, representing ~1 in 10,000 nucleated cells. Although not immortal, they have the ability to expand manyfold in culture while retaining their growth and multilineage potential. Pittenger et al. (Science 284, 143 (1999)) discloses that isolated mesenchymal (stem) cells were uniformly positive for SH2, SH3, CD29, CD44, CD71, CD90, CD106, CD120a, CD124, and many other surface proteins, while the mesenchymal cells were negative for other markers of the hematopoietic lineage, including the lipopolysaccharide receptors CD14, CD34, and the leukocyte common antigen CD45. MSCs are identified by the expression of many molecules including CD44 and CD105 and are negative for the hematopoietic markers CD34, CD45, and CD14.

It was reported that amniotic mesenchymal stromal cells and human chorionic mesenchymal stromal cells could be isolated from placenta. The surface antigen expression of these cells is given in Table A below, showing that they cannot express CD45, CD34, CD14 and HLA-DR (Parolini et al., *Stem Cells* 26: 300-311, 2008).

TABLE A

Specific antigen expression at passages 2-4 for amniotic mesenchymal stromal cells and human chorionic mesenchymal stromal cells

| Positive (≥95%) | Negative (≤2%) |
|---|---|
| CD90 | CD45 |
| CD73 | CD34 |
| CD105 | CD14 |
|  | HLA-DR |

Caplice (U.S. Pat. No. 7,790,453 B2) taught blood-derived, adult smooth muscle progenitor cells which were positive for CD34. However, the smooth muscle progenitor cells disclosed by Caplice are not characterized as mesenchymal stromal stem/progenitor cells and said progenitor cells have limited differentiation potential.

Lucas et al. (U.S. Pat. No. 7,259,011 B2) taught isolated human pluripotent adult stem cells (PPASCs) expressing CD13, CD34, CD56, and CD117. The PPASCs according to Lucas et al. did not express CD10, CD14, and stage specific embryonic antigen SSEA2. The PPASCs are not characterized as mesenchymal stromal stem/progenitor cells, either.

Hariri (U.S. Pat. No. 7,468,276 B2) taught isolated human placental stem cells that are OCT4$^+$ and CD34$^+$. The human placental stem cells disclosed by Hariri were SSEA3$^-$ and SSEA4$^-$. The human placental stem cells of Hariri were not characterized as mesenchymal stromal stem/progenitor cells.

Edinger et al. (US 2008/0206343 A1) discloses non-adherent, CD34$^+$CD45$^-$ stem cells isolated from placenta. The placental stem cells according to Edinger et al. are non-adherent, and thus were not mesenchymal.

For tissue engineering, an enriched population of multipotent stem cells that are juvenile and prolonged self-renewal are desired.

SUMMARY OF THE INVENTION

Accordingly, the present invention provides a plurality of embryonic stem cell-like precursor cells, which is an enriched population of multipotent human mesenchymal common progenitor cells (MCPCs). The cells are isolated from a human somatic tissue by a systemic screening of human mesenchymal stromal stem/progenitor cells followed by a cell sorting by a cell antigen selected from the group consisting of CD34, CD117, CD133, CD201, GloboH and combination thereof, and cultured in a medium supplemented with at least one or more steroids, and one or more growth factors. It was unexpectedly found in the invention that a population of multipotent human mesenchymal common progenitor cells (called as "MCPCs") expressed CD34, which is different from known human mesenchymal stromal (stem) cells as not expressing CD34. The MCPCs cells of the invention exhibited sphere-like clonogenicity in early passages and expressed multipotent embryonic stem cells (ESCs) like characteristics.

In one aspect, the invention provides an enriched population of multipotent human mesenchymal common progenitor cells (MCPCs), which are identified as mesenchymal stromal stem/progenitor cells having at least the following characteristics: CD14$^+$, CD34$^+$, CD117$^+$, CD133$^+$ (AC133$^+$), CD201$^+$, Nestin$^+$, SSEA3$^+$, SSEA4$^+$, and GloboH$^+$.

In another aspect, the invention provides a method for producing the enriched population of multipotent human MCPCs according to the invention, comprising isolating from a human somatic tissue by a systemic screening of human mesenchymal stromal stem/progenitor cells followed by a cell sorting by a cell antigen selected from the group consisting of CD34, CD117, CD133, CD201, GloboH and combination thereof, and culturing in a medium supplemented with at least one or more steroids selected from the group consisting of a corticosteroid and cholesterol and one or more growth factors selected from the group consisting of epidermal growth factor (EGF), fibroblast growth factor (FGF), insulin-like growth factor (IGF), insulin, platelet-derived growth factor (PDGF), IL-6, and thrombopoietin (TPO).

In one further aspect, the invention provides a composition comprising the enriched population of multipotent human MCPCs according to the invention encapsulated in alginate.

In yet aspect, the invention provides a feeder cell layer for stem cell culture comprising the enriched population of multipotent human MCPCs of the invention.

In further yet aspect, the invention provides a stem cell niche comprising the enriched population of multipotent human MCPCs according to the invention seeded on a scaffold.

BRIEF DESCRIPTION OF THE DRAWINGS

The foregoing summary, as well as the following detailed description of the invention, will be better understood when read in conjunction with the appended drawing.

FIG. 1A is a phase contrast image of AM-MSCs-CD34$^+$ cells. FIG. 1B is a phase contrast image of AM-MSCs-CD34$^-$ cells.

FIG. 2 shows the profiling of cell surface marker of AM-MSCs-CD34$^+$ and AM-MSCs-CD34$^-$ cells; wherein FIG. 2A shows the expression of CD29, CD44, CD73, CD90, CD105, CD31, CD56, EGFR, and PDGFR; and FIG. 2B shows the expression of CD34, CD117, CD133, SSEA1, SSEA3, SSEA4, GloboH, and CD201.

FIG. 4B provides TuJ1 (top), GFAP (middle), and DAPI (bottom) immunofluorescence staining images of CD34$^-$ AM-MSC induced neurons; FIG. 4C provides TH (top), MAP2 (middle), and DAPI (bottom) immunofluorescence staining images of CD34$^+$ AM-MSC induced neurons; And FIG. 4D provides TH (top), MAP2 (middle), and DAPI (bottom) immunofluorescence staining images of CD34$^-$ AM-MSC induced neurons.

FIG. 5 shows the cell morphology of human endometrium mesenchymal cells; wherein FIG. 5A is a phase contrast image of EnMSCs-CD34$^+$ cells; and FIG. 5B is a phase contrast image of EnMSCs-CD34$^-$ cells.

FIG. 6B provides Troponin T (top), myosin heavy chain (MHC) (middle), and DAPI (bottom) immunofluorescence staining images of CD34$^-$ EnMSCs after cardiomyogenic induction.

DESCRIPTION OF THE EMBODIMENTS

Figure 1:
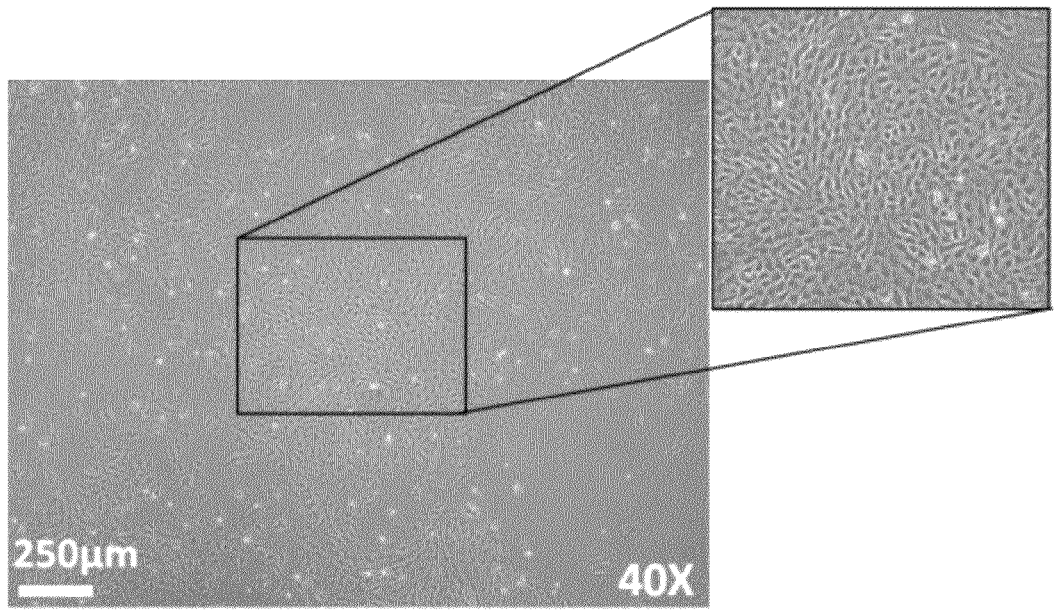
FIG. 1 shows the cell morphology of human placenta amnionic mesenchymal cells.
Figure 1:
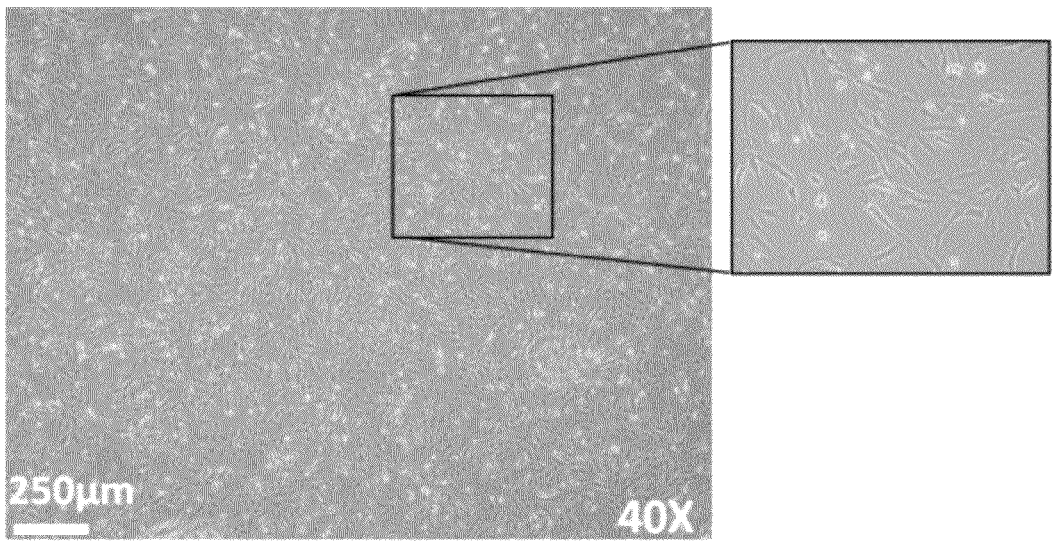

As used herein, the article "a" or "an" means one or more than one (that is, at least one) of the grammatical object of the article, unless otherwise made clear in the specific use of the article in only a singular sense.

According to the invention, it is unexpectedly found that a plurality of precursor cells are isolated from human somatic tissues, and identified as mesenchymal stromal stem/progenitor cells expressing at least CD14, CD34, CD117, CD133 (AC133), CD201, Nestin, SSEA3, SSEA4, and GloboH (called as "MCPCs"). The MCPCs may be obtained by a method comprising the steps of isolating from a human somatic tissue by a systemic screening of human mesenchymal stromal stem/progenitor cells followed by a cell sorting by a cell antigen selected from the group consisting of CD34, CD117, CD133, CD201, GloboH, and combination thereof, and culturing in a medium supplemented with at least one or more steroids selected from the group consisting of a corticosteroid, cholesterol, and combination thereof, and one or more growth factors selected from the group consisting of epidermal growth factor (EGF), fibroblast growth factor (FGF), insulin-like growth factor (IGF), insulin, platelet-derived growth factor (PDGF), IL-6, thrombopoietin (TPO), and combination thereof. The MCPCs of the invention adhere to a tissue culture surface, which is different from the CD34$^+$, CD45$^-$ placental stem cells as disclosed in Edinger et al. (US 2008/0206343 A1).

The MCPCs of the invention can be isolated from human somatic tissues including but not limited to neonatal placenta (e g amnion, chorion, and umbilical cord), endometrium, gingival, bone marrow, and adipose. Preferably, the MCPCs are isolated from placenta, endometrium, and gingival. More preferably, the MCPCs are isolated from placenta amniotic tissue. According to the invention, the MCPCs isolated from placenta amniotic tissue are called as AM-MSCs-CD34$^+$ cells; the MCPCs isolated from endometrium are called as EnMSCs-CD34$^+$ cells; and the MCPCs isolated from gingival are called as GMSCs-CD34$^+$ cells. Specifically, AM-MSCs-CD34$^+$ cells, EnMSCs-CD34$^+$ cells, and GMSCs-CD34$^+$ cells have consistent profiling of cell surface markers expression. In the invention, the MCPCs exhibited sphere-like clonogenicity in early passages and expressed multipotent embryonic stem cell (ESCs) like characteristics in vitro. Morphologically, the MCPCs of the invention are shorter than CD34$^-$ MSCs. Specifically, the MCPCs of the invention have a higher growth rate as compared to CD34$^-$ MSCs or unsorted MSCs, indicating that MCPCs of the invention are more proliferative and younger.

According to the invention, the MCPCs homogenously express embryonic (e.g. Oct-4, Nanog, Rex-1, Sox-2), stemness (e.g. CD117, CD34, CD44) surface antigens, in addition to present various lineage markers, including MSC (e.g. CD29, CD90, CD73, CD105, CD106), hem-angiogenic (e.g. AC133, CD34), myo-nurogenic (e.g. CD54, Nestin, NSE). Further, the MCPCs of the invention are prolonged self-renewal. According to some embodiments of the invention, the MCPCs (e.g., AM-MSCs-CD34$^+$ cells) could retain their specific cell marker expression as CD34, CD54, CD117, and AC133 positive, and their MSC marker expression even after 20 passages.

Accordingly, the invention provides an enriched population of multipotent human mesenchymal common progenitor cells (MCPCs), which are identified as mesenchymal stromal stem/progenitor cells which have at least the following characteristics: CD14$^+$, CD34$^+$, CD117$^+$, CD133$^+$ (AC133$^+$), CD201$^+$, Nestin$^+$, SSEA3$^+$, SSEA4$^+$, and GloboH$^+$.

According to the invention, the enriched population of multipotent human MCPCs further have at least one of the following characteristics: CD44$^+$, CD54$^+$, CD56$^+$, CD105$^+$, CD146$^+$, and PDGFR$^+$. In one embodiment of the invention, the enriched population of multipotent human MCPCs are identified as mesenchymal stromal stem/progenitor cells, having the following characteristics: CD14$^+$, CD34$^+$, CD117$^+$, CD133$^+$ (AC133$^+$), CD201$^+$, Nestin$^+$, SSEA3$^+$, SSEA4$^+$, GloboH$^+$, CD44$^+$, CD54$^+$, CD56$^+$, CD105$^+$, CD146$^+$ and PDGFR$^+$.

According to the invention, the enriched population of multipotent human MCPCs have the potentials to differentiate into cells or tissues of ectodermal lineage, mesodermal lineage, and endodermal lineage. In one embodiment of the invention, AM-MSCs-CD34+ cells were examined and found that they were multipotent in differentiation of various types of somatic cells, including endoderm, mesoderm, or ectoderm cells.

In one embodiment of the invention, the enriched population of multipotent human MCPCs have the potentials of adipogenic differentiation, osteogenic differentiation, chondrogenic differentiation, neurogenic differentiation, cardiomyogenic differentiation, endothelial differentiation, and hepatic differentiation.

In addition, the invention provides a method for producing an enriched population of multipotent human MCPCs, comprising isolating from a human somatic tissue by a systemic screening of human mesenchymal stromal stem/progenitor cells and a cell sorting by a cell antigen selected from the group consisting of CD34, Nestin, CD117, CD133 and combination thereof; and culturing in a medium supplemented with at least one or more steroids and one or more growth factors.

As used herein, the term "steroid" refers to a type of organic compound that contains a specific arrangement of four cycloalkane rings that are joined to each other. In the invention, the steroid used in the medium according to the method may be one selected from the group consisting of a corticosteroid, cholesterol and combination thereof.

As used herein, the term "corticosteroid" refers to a class of steroid hormone. Examples of corticosteroid include but are not limited to a group A corticosteroid (e.g. hydrocortisone, hydrocortisone acetate, and cortisone acetate), a group B corticosteroid (e.g. triamcinolone acetonide, triamcinolone alcohol, and mometasone), a group C corticosteroid (e.g. betamethasone, betamethasone sodium phosphate, and dexamethasone), and a group D corticosteroid (e.g. hydrocortisone-17-valerate, aclometasone dipropionate, and hydrocortisone-17-butyrate).

The term "growth factor" as used herein refers to a naturally occurring substance capable of stimulating cellular growth, proliferation and cellular differentiation, which can regulate a variety of cellular processes, and typically act as signaling molecules between cells. In the invention, the growth factor used in the medium according to the method may be one or more selected from the group consisting of epidermal growth factor (EGF), fibroblast growth factor (FGF), insulin-like growth factor (IGF), insulin, platelet-derived growth factor (PDGF), IL-6, thrombopoietin (TPO), and combination thereof.

According to some embodiments of the invention, the medium may be further supplemented with and one or more vitamins.

As used herein, the term "vitamin" refers to a nutrient in tiny amounts by an organism. In the invention, examples of vitamins include but are limited to vitamin A, vitamin B-complex, vitamin E, biotin, p-aminobenzoic acid, menadione, and combination thereof.

In the invention, the medium may be also supplemented with one or more compounds selected from the group consisting of uracil, sodium acetate, ribose, Guanine HCl, deoxyribose, adenosine, adenine sulphate, ferric nitrate and combination thereof.

In preferred embodiments of the invention, the cell sorting is performed by using fluorescence-activated cell sorting (FACS) flow cytometry. Preferably, the cell sorting is a CD34, CD117, CD133, CD201, or GloboH cell antigen FACS.

According to the invention, the MCPCs may be encapsulated in alginate to form a composition.

According to the invention, a feeder cell layer for stem cell culture is provided as well. The feeder cell layer comprises the enriched population of multipotent human MCPCs of the invention. Alternatively, the enriched population of multipotent human MCPCs may be seeded on the scaffold to form a stem cell niche.

Accordingly, the invention provides a better source of ESC-like clonogenic stem cells that are derived from non-embryonic neonatal or adult tissue and multipotent in differentiation to various types of cells, than known sources, such as ESCs. The MCPCs of the invention were found to be of proliferative ability and differentiation potentials. They are of a great potential to be used for clinical regenerative therapies. The invention is further described in the following non-limiting examples.

Human tissues used in the following examples were obtained using a protocol approved by Institutional Review Board of Cathay General Hospital & Taipei Medical University Institutional Review Board.

EXAMPLE 1

Preparation and Characterization of AM-MSCs-CD34+ Cells

Amnionic Mesenchymal Cell Isolation
(1) Isolation of Amnion Membrane:
Amnion membrane (about 300 cm², n=9) was stripped from chorion, washed in 3×150 ml changes of 1× Hank's buffer to remove blood.
(2) Removal of the Amnionic Epithelial Cells:
To deplete the amnionic epithelial cells (Am-EpCs), washed amnion membrane was cut into 2-3 cm² fragments and incubated in 100 ml of 0.1% Trypsin-EDTA (Sigma; St Louis, Mo.) with 1× Hanks balanced salt solution (Gibco; CAT#14185-052; Grand Island, N.Y.) for an about 250 cm² membrane, with 4 times of each 15 min reactions in water bath, at 37° C.
(3) Collection of Clonogenic Amnionic Mesenchymal Stromal Cells (AM-MSCs):
For the amnionic mesenchymal cells (AM-MSCs) isolation, the Am-EpCs depleted amnion membrane was subjected to wash with Hank's buffer one time and digested with collagenase 1A at 37° C. for 45-60 minutes. An appropriate volume of Hank's buffer and a 40 μm nylon cell strainer were used to collect the clonogenic AM-MSCs.
(4) Incubation of AM-MSCs:
After a 170 g centrifugation, AM-MSCs were plated in CELL-BIND T75 flasks at a density of $5 \times 10^4$ cells per cm² and incubated in a 5% $CO_2$, 37° C. The collected AM-MSCs were incubated in a medium containing Medium 199 (the M199 conditioned medium) [(Lonza CAT#12-118F; Switzerland), supplemented with fetal bovine serum (FBS), epidermal growth factor (EGF), and hydrocortisone. Fresh medium were changed in every 3~4 days during the purification incubation, and cells expanded to 80% confluence in 7 days. The attached culturing cells were harvested with 0.1% Trypsin-EDTA, and split into the new passage culture with a seeding density of $1 \times 10^5$ cells per T75 flask.

Alternatively, the collected CM-MSCs can be cultured in RPMI-1640 (GIBCO; Grand Island, N.Y.) supplemented with fetal bovine serum (FBS) (10%), sodium pyruvate (0.1 mM), basic fibroblast growth factor (bFGF), and EGF (10 ng/ml). Cells were split when they reached to 70~80% confluence, the culture medium was changed every 3~4 days.

Flow Cytometry Analysis

For FACS analysis, freshly harvested AM-MSCs were trypsinized and incubated with aliquot florescence (FITC or PE) conjugated monoclonal antibodies (mAbs), suggested by the manufacturer, for 30 minutes at 4° C. in 100 μl phosphate buffer. Cell markers were tested including for the mesenchymal stem cell (MSC) lineage (CD29, CD90, CD73, CD105, CD106, Vimentin), stemness (CD34, CD44, CD117), hem-angiogenic (AC133, CD34), myo-neurogenic (CD54, Nestin), and myofibroblast markers (Vimentin, alpha smooth muscle actin). Cells were analyzed using a FACSCanto flow cytometry system (BD Bioscience, San Jose, Calif.). The flow-cytometric data were processed with FCS Express V3 software (De Novo; Canada).

Flow Cytometry Sorting

For isolation of the CD34+ AM-MSCs sub-population, the expanded primary AM-MSCs cultured at passages 2-3 were used to label with CD34 antibody. Up to $3 \times 10^6$ cells were sorted by a FACS Aria flow cytometry (BD Bioscience, San Jose, Calif.) following the manufacture's instruction. CD34 positive (CD34+) and CD34 negative (CD34−) cells were then analyzed, sorted, and collected.

Figure 2:
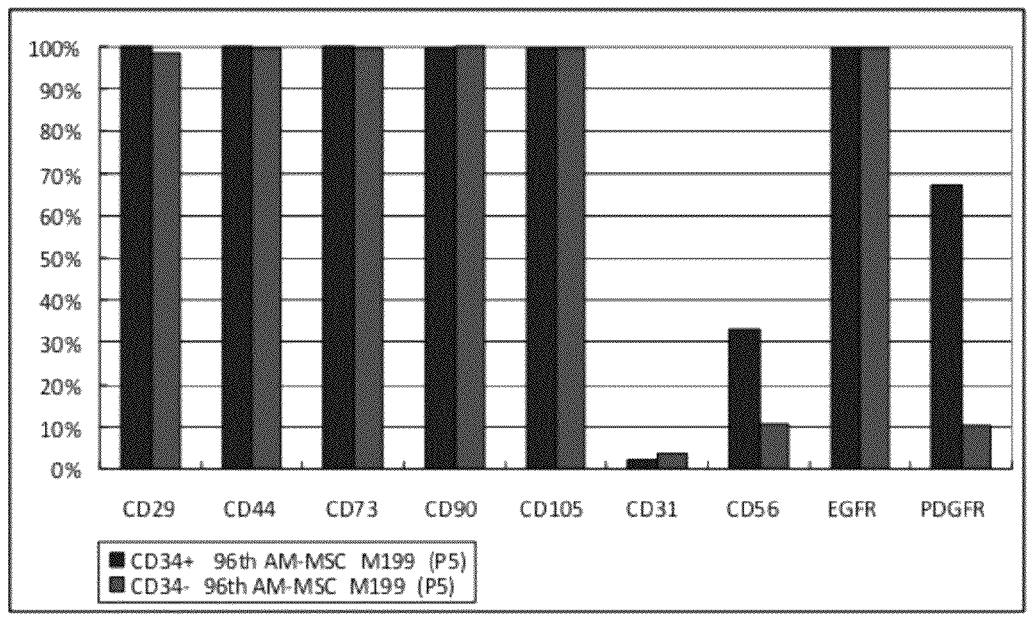
Figure 2:
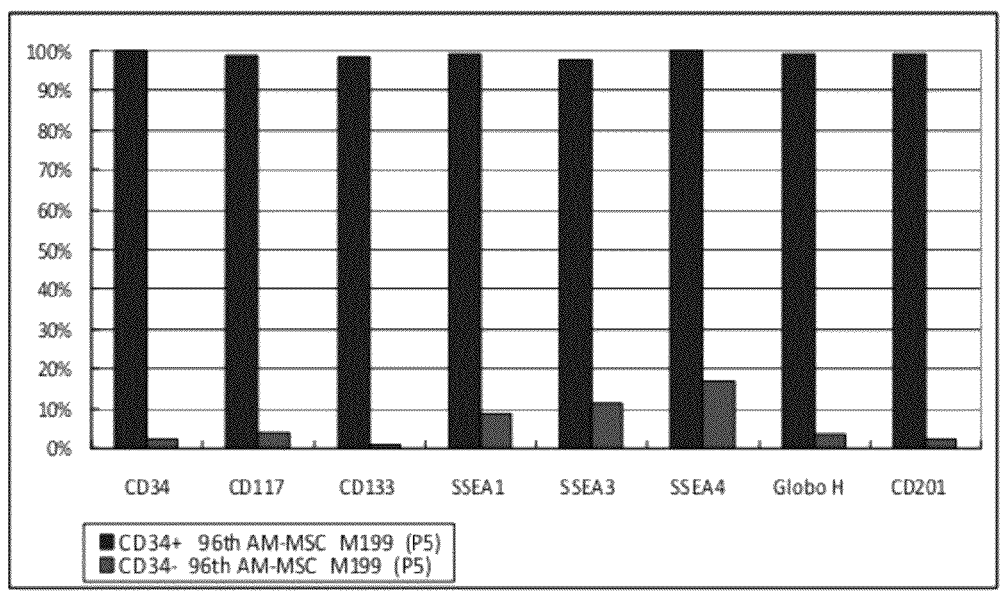

In brief, $3-4 \times 10^6$ harvested third passage AM-MSCs were trypsinized and labelled with PE-conjugated CD34 suggested by the manufacturer, for 15 minutes at room temperature in 100 μl phosphate buffer. Then filtered cells through a 40 μm nylon cell strainer (Becton, Dickinson and Company CAT#352235) and sorting AM-MSCs-CD34+ and AM-MSCs-CD34− populations with BD FACS Aria. After sorting, the AM-MSCs-CD34+ and AM-MSCs-CD34− populations were re-analyzed for the positive fraction and expanded in the M199 conditioned medium as described above or the RPMI conditioned medium. The cell morphology of AM-MSCs (passage 3) are given in FIG. 1, wherein the shape of AM-MSCs-CD34+ cells (FIG. 1A) is shorter than AM-MSCs-CD34− cells (FIG. 1B) and both showed stable in later passages. The initial doubling time of AM-MSCs-CD34− cells is about 42 hours, which is longer than that of AM-MSCs-CD34+ at being 34 hours. The CD34 expression of AM-MSCs would be checked for each five passages in the following days. After CD34+ sorting 20 passages, CD34+ AM-MSC could still retain their specific cell marker expression as CD34, CD54, CD117, and CD133 (AC133) positive and their MSC marker expression. It was found that the high expression each of CD and gene markers other than CD34 could be observed in the cells at each passage, but the expression of CD34 (50~60%) of the cells at passage 1 was less than those of passages 3 or 9 (about 100%). Both CD34+ and CD34− sorted AM-MSC expressed CD29, CD44, CD73, CD90, CD105, EGFR positive, and CD31 negative. However, CD34+ AM-MSC expressed more CD56 and PDGFR than CD34− AM-MSC. See FIG. 2A. Further, CD34+ AM-MSC could express more CD117, CD133, SSEA1, SSEA3, SSEA4, Globo H, and CD201 than CD34− AM-MSC (FIG. 2B). Specific gene expression was also examined by RT-PCR (data not shown). The results show that AM-MSCs-CD34+ cells express "early genes" including Sox-2, Oct-4, Rex-1, and Nanog, ectodermal lineage genes, e.g. neurogenic differentiation markers including Nestin, NSE, NFM, NCAM, MAP2, mesodermal lineage genes, e.g. cardiomyogenic differentiation markers including MyoD, GATA-4, and MLC-2a, and endodermal lineage genes, e.g. hepatic differentiation makers including Albumin and HGF.

EXAMPLE 2

Induction of Differentiation (1) Vasculogenic Differentiation

The AM-MSCs-CD34+ cells at the number of $2 \times 10^5$ at passage 5 were used for the vasculogenic differentiation induction. Harvested cells were cultured in EGM-2 medium (Cambrex) for a 7 days induction. Analysis of the capillary formation was performed using Matrigel (BD Biosciences). Specifically, after the induction culture, the AM-MSCs-CD34+ were trypsinized and plated onto Matrigel coated (Matrigel: M199=1:1) 24 well cluster, with a cell density of $10^5$ cells per well. Capillary-like structures were observed by optical microscopy after 2, 4, 24, and 48 hours in the following 3 days.

(2) Cardiomyogenic Differentiation

Sorted AM-MSCs-CD34+ cells at passages 4-6 were harvested for induction of cardiomyogenic differentiation. The AM-MSCs-CD34+ cells were incubated overnight in the growth medium [EGM-2:M199 (v:v=1:3) supplemented with 10% FBS, and MEM nonessential amino acids (1×) (GIBCO)]. On the next morning, cells were transferred into the cardiomyogenic differentiation medium, [IMDM (GIBCO): Ham's F12 nutrient mixture with GlutaMAX-1 (GIBCO) (v:v=1:1) supplemented 2% horse serum (GIBCO), 1×MEM nonessential amino acids, 1× insulin-transferrin-selenium (GIBCO)] with a cell density of $10^4$ per cm$^2$. After 6-8 hours, a cardiomyocytic differentiation agent, 5-azacytidine (Sigma) was added into the medium to make a 5 μM final concentration. 4 ul/ml of 5-azacytidine (0.25 mM) stock solution was added into the differentiation medium daily, and changed back to the differentiation medium without 5-azacytidine on the day 4. On day six of the differentiation assay, ascorbic acid ($10^{-4}$ M) (Sigma) and TGF-β1 (1 ng/ml) (PeoproTech) were added to the medium. From this point forward, ascorbic acid and TGF-β1 were supplemented every other days and twice weekly, respectively. The medium were changed every 2~3 days, depending on the medium pH changes. Cell debris should be removed by PBS washes, when medium changes. The Cardiomyogenic AM-MSCs-CD34+ cells were fixed for histochemical staining after 28-day differentiation culture. By a 5-azacytidine myogenic induction, CD34+ AM-MSCs (P5) transdifferentiated easily into cardiomyocytes expressing MyoD, GATA-4, MLC-2a genes (data not shown). After cardiomyogenic differentiation 28 days and examined by histochemical staining, both CD34+ and CD34− AM-MSCs expressed myosin heavy chain (MHC), but only induced CD34+ AM-MSCs formed typical cardiomyocyte morphology and expressed terminal differentiated marker Troponin T (data not shown).

(3) Hepatic Differentiation

The expressions of hepatic differentiation cell markers were given in Table 1 below.

TABLE 1

Expressions of hepatic differentiation cell markers of AM-MSCs-CD34+ cells (passage 6).

| | Cell Marker | AM-MSCs-CD34+ | Control |
|---|---|---|---|
| Gene | DAPI | +++ | +++ |
| | Cy3 (Albumin) | +++ | − |
| | FITC (Cytokeratin) | +++ | − |
| Protein | GAPDH | +++ | +++ |
| | Albumin | +++ | − |
| | HGF | ++ | − |

(4) Adipogenic, Osteogenic, and Chondrogenic Differentiation

The AM-MSCs-CD34$^+$ cells obtained by the method as mentioned in Example 1 and expanded passages 5-6 were used for multi-lineage differentiation inductions. The adipogenic, osteogenic, chondrogenic, and neurogenic differentiation protocols were used by the methods given below.

The AM-MSCs or AM-MSCs-CD34$^+$ pre-conditioning in Dulbecco's modified Eagle's medium (DMEM/LG, GIBCO) supplemented with 10% FBS (Hyclone) were used for the lineage differentiation cultures shown as following:
1) Adipogenesis (AM): DMEM/LG medium supplemented with 10% FBS, 0.5 mM isobutyl-methylxanthine, 1 μM dexamethasone, 10 μM insulin, 200 μM indomethacin.
2) Osteogenesis (OM): DMEM/LG medium supplemented with 10% FBS, 0.1 μM dexamethasone, 50 μM ascorbate-2-phosphate, 10 mM β-glycerolphosphate.
3) Chondrogenesis (CM): DMEM/LG medium supplemented with 1% FBS, 6.25 μg/ml insulin, 10 ng/ml TGF-β1 (R&D), 50 nM ascorbate-2-phosphate.
4) Neurogenesis (NM): DMEM/LG medium supplemented with 5 μg/ml insulin, 200 μM indomethacin, 0.5 mM isobutyl-methylxanthine. (Reagents used above for differentiation were all from Sigma; St. Louis, Mo.)

For adipogenic, osteogenic, and neurogenic differentiation, the cell density was $3 \times 10^4$ cells/cm$^2$. For chondrogenic differentiation, a higher cell density of $1-2 \times 10^5/10$ μl was used for chondrosphere formation. Medium was changed every three to four days for all differentiation assays, and cells were fixed for histochemical staining after 14 days of adipogenic, osteogenic, chondrogenic differentiation. After 14 days, intracellular oil droplets were formed under Oil Red O stain, and calcified extracellular matrix was present and positive for von Kossa staining (data not shown). In chondrogenic differentiation, AM-MSCs-CD34$^+$ cells formed cartilage ball in 3 days. AM-MSCs-CD34$^+$ cells cultured in neurogenic differentiation medium (Zuk's protocol, P4, Day 21) exhibited neural morphology and expressed neural markers including Nestin, NSE, NFM, NCAM, and MPA2, while AM-MSCs-CD34$^-$ cells did not (data not shown).

(5) Neurogenic Differentiation

Figure 3:
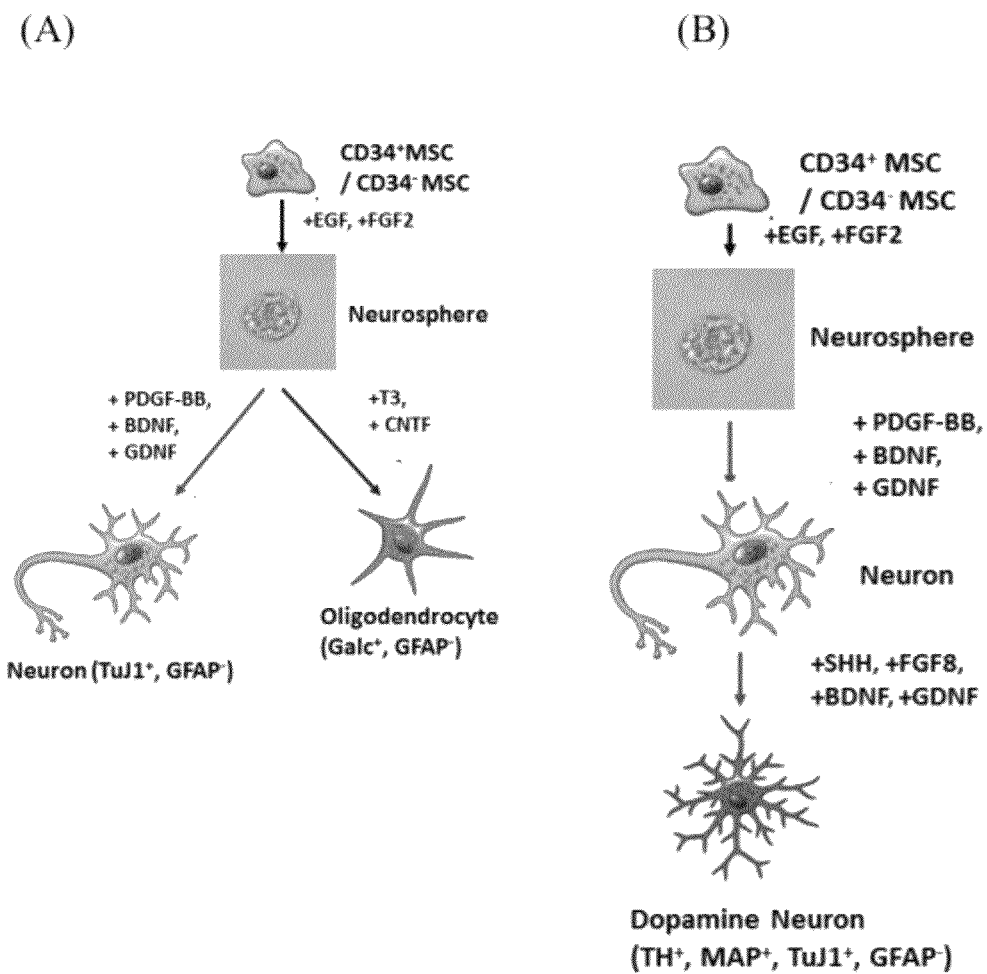
FIG. 3A provides a schematic illustration of neural and oligodendrocyte differentiation of CD34 sorted MSCs.
FIG. 3B provides a schematic illustration of dopaminergic neuron differentiation of CD34 sorted MSCs.

Step1: Neurosphere Formation: Cells were seeded at a density of 1000 per well with neurosphere medium (NS medium). NS Medium: DMEM/HG/F12 (1:1)+1×B27+20 ng/ml EGF+20 ng/ml FGF2+2 μg/ml Heparin. Primary neurospheres (selecting mainly floating neurospheres) larger than 75 um were counted after 7 days in vitro. Step2: Neural Differentiation Assay: Dissociated neurospheres to single cells by trypsin-EDTA solution and culture the cells with: DMEM/F12+5% FBS for 24 hrs. These cells were treated with specific neural cell differentiation medium. The medium used for neuronal differentiation was DMEM/F12 supplemented with 2% FBS, 10 ng/ml PDGF, 50 ng/ml BNDF, and 50 ng/ml GDNF. FIG. 3A is a schematic illustration of neural and oligodendrocyte differentiation of CD34 sorted MSCs. FIG. 3B is a schematic illustration of dopaminergic neuron differentiation of CD34 sorted MSCs.

Figure 4:
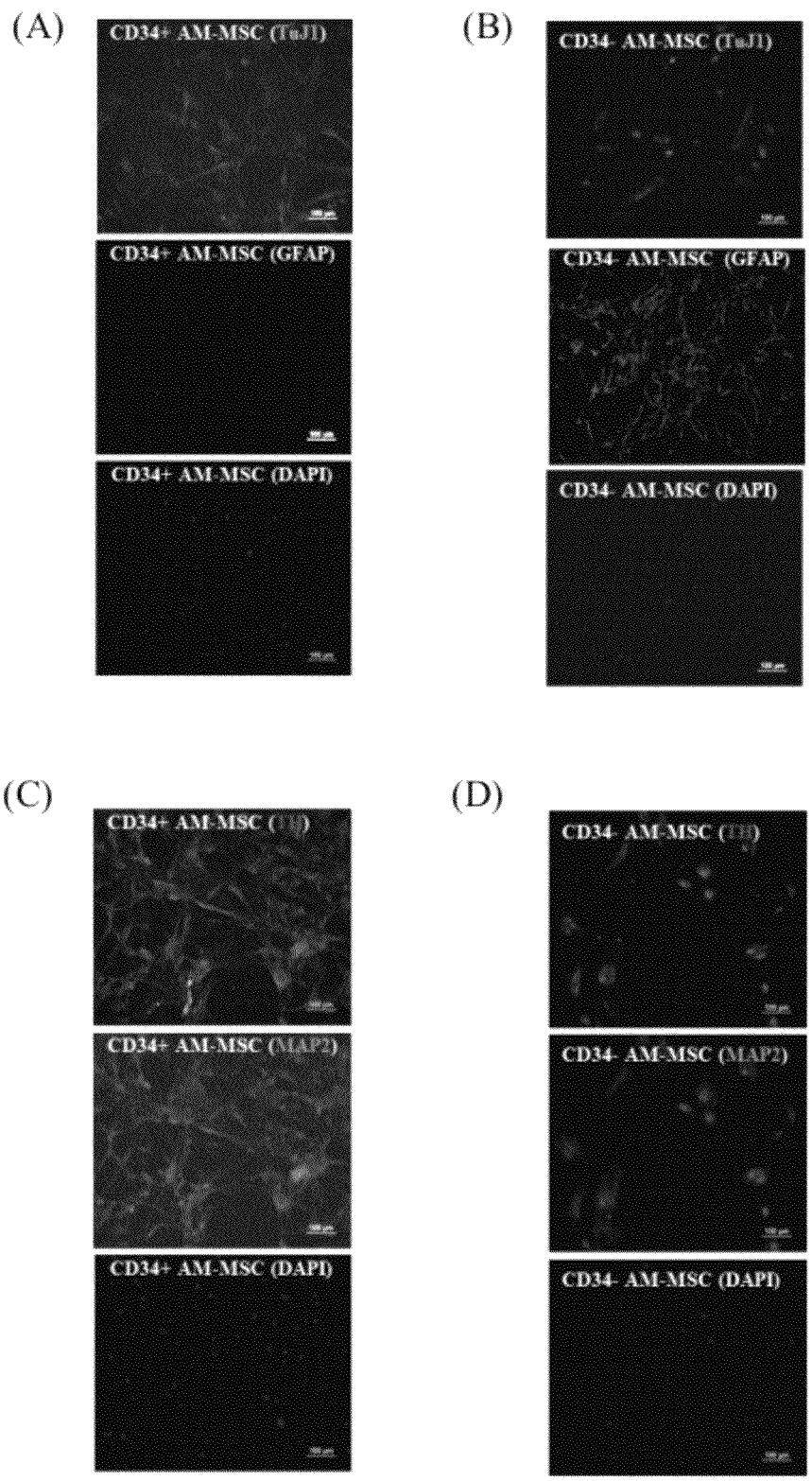
FIG. 4 shows TuJ1, TH, and MAP2 expression of CD34$^+$ or CD34$^-$ AM-MSC after dopaminergic neuron induction, wherein FIG. 4A provides TuJ1 (top), GFAP (middle), and DAPI (bottom) immunofluorescence staining images of CD34$^+$ AM-MSC induced neurons.

After 7 to 9 days, the differentiation capacity was verified by using immunofluorescence staining (GFAP conjugated with FITC, Hochest 33258, and TuJ1 conjugated with rhodamine). After primary neurosphere formation, CD34$^+$ and CD34$^-$ AM-MSC both expressed TuJ1 (neuron specific marker). However, the GFAP (glia specific marker) expression was dim for CD34$^+$ AM-MSC induced neurons. On the other hand, some CD34$^-$ AM-MSC induced neuron expressed GFAP, which suggests that some induced CD34$^-$ AM-MSC cells differentiate into neurons while some of them differentiate into glia cells. In B27 induction, CD34$^+$ AM-MSC expressed Galc, and TuJ1, but not GFAP. For dopaminergic neuron differentiation, as detected by immunofluorescence staining, CD34$^+$ AM-MSC induced neurons were TuJ1, TH, and MAP2 positive, while only a small population of CD34$^-$ AM-MSC induced neurons expressed said markers (FIG. 4).

(6) Conclusion

CD34$^+$ AM-MSCs expressed early genes and showed multipotent differentiation potential. Specific gene expression of CD34$^+$ AM-MSCs is provided in Table 2 below.

TABLE 2

Summary of CD34$^+$ AM-MSCs gene expression.
CD34$^+$ AM-MSCs

| Early Genes | | Ectoderm (Neurogenic Differentiation) | | Mesoderm (Cardiomyogenic Differentiation) | | Endoderm (Hepatic Differentiation) | |
|---|---|---|---|---|---|---|---|
| Sox-2 | + | Nestin | + | MyoD | + | Albumin | + |
| Oct-4 | + | NSE | + | GATA-4 | + | HGF | + |
| Rex-1 | + | NFM | + | MLC-2a | + | — | − |
| Nanog | + | NCAM | + | — | − | — | − |
| — | − | MAP2 | + | — | − | — | − |

EXAMPLE 3

EnMSCs-CD34$^+$ cells, GMSCs-CD34$^+$ cells, and CD34$^+$ MSCs Enriched from Other Somatic Tissues Primary endometrial and gingival tissues were collected from donors from Taipei medical hospital and Dr. Wells Dental clinic follows the IRB guide line. EnMSCs and GMSCs were obtained from endometrial and gingival tissues, respectively, by similar process set forth in Example 1. EnMSCs and GMSCs were then subject to CD34 sorting.

Figure 5:
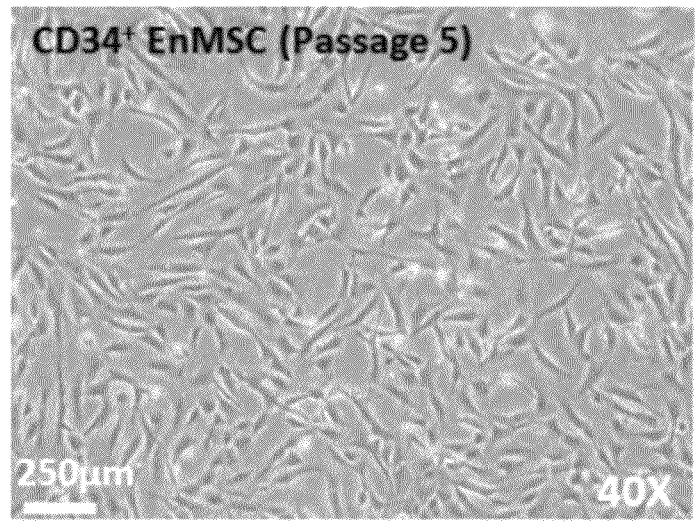
Figure 5:
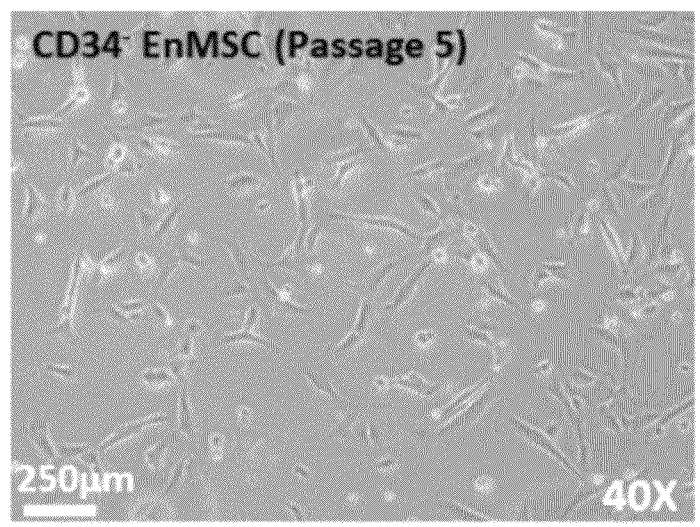

Phase contrast images of CD34 sorted human endometrium derived mesenchymal stem cells (P5) are given in FIG. 5. The morphology of EnMSCs-CD34$^+$ cells was very similar to AM-MSCs-CD34$^+$. Further, as provided in Table 3 below, AM-MSCs-CD34$^+$ cells, EnMSCs-CD34$^+$ cells, and GMSCs-CD34$^+$ cells were identified as having consistent profiling of cell surface marker expression. Specifically, the mesenchymal common progenitor cells (MCPCs) of the invention were CD14$^+$, CD34$^+$, Nestin$^+$, CD117$^+$, CD133$^+$ (AC133$^+$), SSEA3$^+$, and SSEA4$^+$. Further, the MCPCs of the invention were also characterized as CD44$^+$, CD54$^+$, CD105$^+$, CD146$^+$, or PDGFR$^+$.

TABLE 3

Cell surface markers expression of MCPCs and CD34$^-$ MSCs.

| | AM-MSCs (P4) | | EnMSCs (P4) | | GMSCs (P4) | |
|---|---|---|---|---|---|---|
| | CD34+ | CD34− | CD34+ | CD34− | CD34+ | CD34− |
| CD29 | +++ | +++ | +++ | +++ | +++ | +++ |
| CD44 | +++ | +++ | +++ | +++ | +++ | +++ |
| CD73 | +++ | +++ | +++ | +++ | +++ | +++ |
| CD90 | +++ | +++ | +++ | +++ | +++ | +++ |
| CD105 | +++ | +++ | +++ | +++ | +++ | +++ |
| EGFR | +++ | +++ | +++ | +++ | +++ | +++ |
| Integrin α2β1 | +++ | +++ | +++ | +++ | +++ | +++ |
| E-cadherin | − | − | − | − | − | − |
| CD34 | +++ | − | +++ | − | +++ | − |
| CD54 | +++ | + | +++ | + | +++ | + |
| PDGFR | ++ | + | ++ | + | ++ | + |
| Nestin | +++ | + | +++ | + | +++ | + |
| CD14 | +++ | − | +++ | − | +++ | − |

TABLE 3-continued

Cell surface markers expression of MCPCs and CD34− MSCs.

| | AM-MSCs (P4) | | EnMSCs (P4) | | GMSCs (P4) | |
|---|---|---|---|---|---|---|
| | CD34+ | CD34− | CD34+ | CD34− | CD34+ | CD34− |
| CD117 | +++ | − | +++ | − | +++ | − |
| AC133 | +++ | − | +++ | − | +++ | − |
| CD146 | +++ | − | +++ | − | +++ | − |

Percentage of FACS markers expression: −: 0~20%, +: 20~40%, ++: 40~80%, +++: 80~100%.

The comparison on cell morphologies and cell doubling times of MCPCs and CD34− MSCs are given in Table 4 below.

TABLE 4

Comparison of cell morphology and cell doubling time.

| | Cell Morphology | Cell Doubling Time |
|---|---|---|
| AM-MSC (CD34+/CD34−) | CD34+: shorter. CD34−: longer and thinner | CD34+: 34 hrs. CD34−: 42 hrs. |
| EnMSC (CD34+/CD34−) | CD34+: shorter. CD34−: longer and thinner | CD34+: 33 hrs. CD34−: 47 hrs. |
| GMSC (CD34+/CD34−) | CD34+: shorter. CD34−: longer and thinner | CD34+: 32 hrs. CD34−: 45 hrs. |

Potentials of endothelial differentiation and chondrogenic differentiation of MCPCs and CD34− MSCs are given in Table 5 below.

TABLE 5

Potentials of endothelial differentiation and chondrogenic differentiation.

| | Endothelial Differentiation | Chondrogenic Differentiation |
|---|---|---|
| AM-MSCs (CD34+/CD34−) | CD34+: CD31+, KDR+, more tube formation. CD34−: CD31+, KDR+, less tube formation. | CD34+: Bigger cartilage ball (Diameter > 2x). CD34−: Little cartilage ball (Diameter < 100 μm). |
| EnMSCs (CD34+/CD34−) | CD34+: CD31+, KDR+, more tube formation. CD34−: CD31+, KDR+, less tube formation. | CD34+: Bigger cartilage ball (Diameter > 2x). CD34−: Little cartilage ball (Diameter < 100 μm). |
| GMSCs (CD34+/CD34−) | CD34+: CD31+, KDR+, more tube formation. CD34−: CD31+, KDR+, less tube formation. | CD34+: Bigger cartilage ball (Diameter > 2x). CD34−: Little cartilage ball (Diameter < 100 μm). |

Comparison of embryonic gene expression of MCPCs and CD34− MSCs are given in Table 6 below. MCPCs of the invention showed stronger embryonic gene expression than CD34− MSCs.

TABLE 6

Comparison of embryonic gene expression

| | Early Gene Detection |
|---|---|
| AM-MSCs (CD34+/CD34−) | CD34+: Sox-2 +++, Oct-4 +++, Rex-1 +++, Nanog +++ CD34−: Sox-2 +++, Oct-4 ++, Rex-1 ++, Nanog ++ |
| EnMSCs (CD34+/CD34−) | CD34+: Sox-2 +++, Oct-4 +++, Rex-1 +++, Nanog +++ CD34−: Sox-2 +++, Oct-4 ++, Rex-1 +++, Nanog ++ |
| GMSCs (CD34+/CD34−) | CD34+: Sox-2 +++, Oct-4 +++, Rex-1 +++, Nanog +++ CD34−: Sox-2 +++, Oct-4 ++, Rex-1 ++, Nanog ++ |

Figure 6:
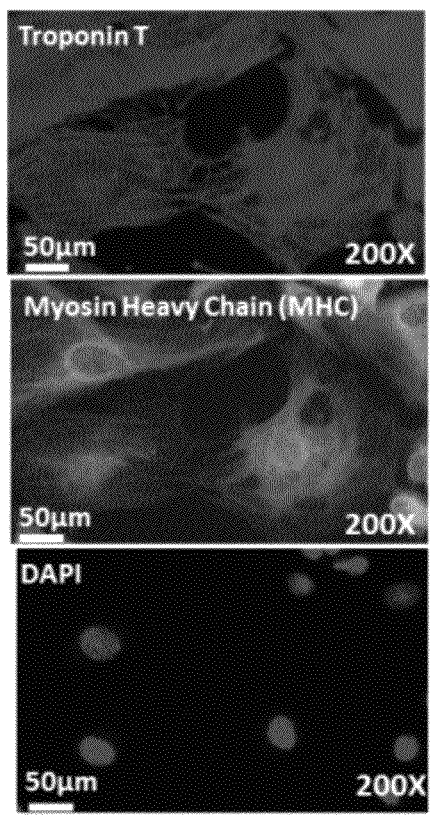
FIG. 6 shows the cardiomyogenic differentiation potentials of EnMSCs-CD34$^+$; wherein FIG. 6A provides Troponin T (top), myosin heavy chain (MHC) (middle), and DAPI (bottom) immunofluorescence staining images of CD34$^+$ EnMSCs after cardiomyogenic induction.
Figure 6:
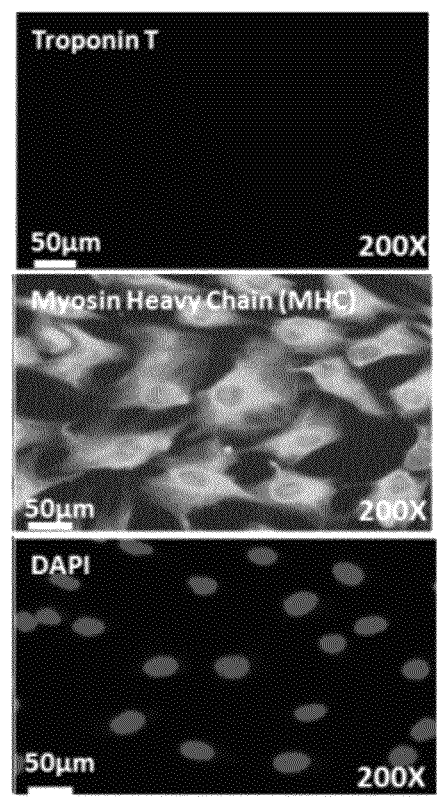

Potentials of neurogenic differentiation and cardiomyogenic differentiation of MCPCs and CD34− MSCs are given in Table 7 below. The cardiomyogenic marker immunofluorescence staining images of EnMSCs are as shown in FIG. 6.

TABLE 7

Potentials of neurogenic differentiation and cardiomyogenic differentiation.

| | Neurogenic Differentiation | Cardiomyogenic Differentiation |
|---|---|---|
| AM-MSCs (CD34+/CD34−) | CD34+: Nestin+, TuJ1+, GFAP−, typical neuron forming CD34−: Nestin+, TuJ1(less+), GFAP− | CD34+: Myosin Heavy Chain+, Troponin T+. CD34−: Myosin Heavy Chain+, Troponin T−. |
| EnMSCs (CD34+/CD34−) | CD34+: Nestin+, TuJ1+, GFAP−, neurosphere-like structure. CD34−: Nestin+, TuJ1+, GFAP− | CD34+: Myosin Heavy Chain+, Troponin T+. CD34−: Myosin Heavy Chain+, Troponin T−. |
| GMSC (CD34+/CD34−) | CD34+: Nestin+, TuJ1+, GFAP−, neurosphere-like structure. CD34−: Nestin+, TuJ1+, GFAP− | CD34+: Myosin Heavy Chain+, Troponin T+. CD34−: Myosin Heavy Chain+, Troponin T−. |

CD34+ MSCs can be enriched from many other somatic tissues according to the method of the invention. Normally, only 2-3% of MSCs are CD34$^+$. After isolated and enriched in culture, percentage of CD34$^+$ MSCs ranging from 15% to 78% depending on which tissue they were isolated from and the donor (See Table 8 below). The culture-enriched CD34$^+$ MSCs can be subject to FACS cell sorting for further enrichment to obtain a population of MSCs enriched with 99% or more CD34+ MSCs.

TABLE 8

Enrichment of Stem/progenitor marker and gene expressions in Human Tissue MSCs

| Marker Tissues | % Enriched % CD34$^+$ MSCs Enrichment in Culture |
|---|---|
| NeoNatal Placenta | 40~70 (~55) |
| Amnion | 48~53 (~50) |
| Chorion | 40~62 (~51) |
| Umbilical Cord | 34~45 (~40) |
| Adult Somatic | 20~78 (~50) |
| Endometrium | 45~78 (~61) |
| Gingiva | 27~35 (~31) |
| Bone Marrow | 20~30 (~25) |
| Adipose | 15~30 (~23) |

EXAMPLE 4

MCPCs as Feeder Cells

MCPCs of the invention were used to prepare a stromal feeder for expansion of hematopoietic stem cells (HSCs). Stromal cells (MS-5, or MSCs) were seeded in plate and wait for confluence to become feeder. 2~4×10$^4$ CD34$^+$ mononuclear cells (MNCs) were co-cultured with feeder in 1 ml HSC medium (X-VIVO10+50 ng/ml SCF+50 ng/ml Flt-3L+ (20 ng/ml)10 U/ml TPO+10 ng/ml IL-6). After 7 days or 14 days, suspension cells were counted and subjected to flow cytometry analysis (for CD34+CD38−, CD34+CD133+, CD34+CXCR4+, etc.).

Figure 7:
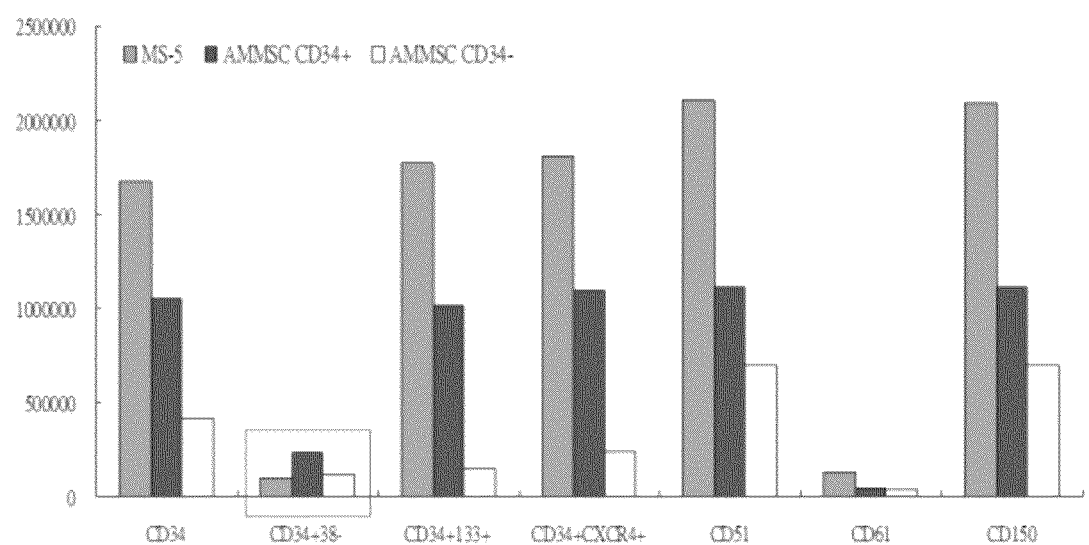
FIG. 7 shows the numbers of expanded hematopoietic stem cells (HSCs) with specific surface marker(s) when co-culturing with murine MS-5 feeder, MSCs-CD34$^+$ feeder, or MSCs-CD34$^-$ feeder.

The results are shown in FIG. 7. When co-culturing with the MCPCs (AM-MSCs-CD34$^+$ cells) feeder, more engrafting CD34+CD38− primitive HSCs were obtained, as compared to murine MS-5 feeder or MSCs-CD34$^-$ feeder.

Although the present invention is illustrated by the above embodiments, these embodiments are not used to limit the present invention. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for producing an enriched population of multipotent human CD34$^+$ mesenchymal common progenitor cells (CD34$^+$ MCPCs), further having at least the following characteristics: CD14$^+$, CD117$^+$, CD133$^+$ (AC133$^+$), CD201$^+$, Nestin$^+$, SSEA3$^+$, SSEA4$^+$ and GloboH$^+$, the method comprising:
    isolating from a human somatic tissue by a systemic screening of human mesenchymal stromal stem/progenitor cells followed by a cell sorting by a cell antigen of CD34, wherein the human somatic tissue is selected from the group consisting of amnion, endometrium and gingival; and
    culturing in a medium comprising EGF and hydrocortisone or a medium comprising bFGF and EGF.

2. The method according to claim 1, wherein the cell sorting is a fluorescence-activated cell sorting (FACS) flow cytometry.

* * * * *